(12) United States Patent
Yamada et al.

(10) Patent No.: US 12,105,055 B2
(45) Date of Patent: Oct. 1, 2024

(54) BACKING MATERIAL FOR ULTRASONIC PROBE, METHOD OF MANUFACTURING SAME, AND ULTRASONIC PROBE

(71) Applicant: MITSUBISHI PENCIL COMPANY, LIMITED, Tokyo (JP)

(72) Inventors: Kunitaka Yamada, Fujioka (JP); Toshiki Oono, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 627 days.

(21) Appl. No.: 17/049,778

(22) PCT Filed: Apr. 1, 2019

(86) PCT No.: PCT/JP2019/014535
§ 371 (c)(1),
(2) Date: Oct. 22, 2020

(87) PCT Pub. No.: WO2019/208118
PCT Pub. Date: Oct. 31, 2019

(65) Prior Publication Data
US 2021/0247364 A1    Aug. 12, 2021

(30) Foreign Application Priority Data
Apr. 26, 2018 (JP) .................. 2018-085396

(51) Int. Cl.
*G01N 29/24* (2006.01)
*C01B 32/05* (2017.01)
(Continued)

(52) U.S. Cl.
CPC ......... *G01N 29/2437* (2013.01); *C01B 32/05* (2017.08); *C04B 35/83* (2013.01);
(Continued)

(58) Field of Classification Search
CPC .... G01N 29/2437; G01N 29/28; C01B 32/05; C04B 35/83; C04B 38/067;
(Continued)

(56) References Cited

U.S. PATENT DOCUMENTS

2005/0275313 A1* 12/2005 Yamashita ............ B06B 1/0622
310/327
2007/0072768 A1* 3/2007 Essaki .................. C04B 38/068
502/413
(Continued)

FOREIGN PATENT DOCUMENTS

CN    103415492 A    11/2013
CN    105286913 A    2/2016
(Continued)

OTHER PUBLICATIONS

Office Action dated Nov. 24, 2021, issued in counterpart CN application No. 201980025011.6, with English translation. (12 pages).
(Continued)

*Primary Examiner* — Tarun Sinha
(74) *Attorney, Agent, or Firm* — WHDA, LLP

(57) ABSTRACT

This backing material for ultrasonic probes substantially comprises porous amorphous carbon.

8 Claims, 1 Drawing Sheet

(51) Int. Cl.
  *C04B 35/83* (2006.01)
  *C04B 38/06* (2006.01)
  *G01N 29/28* (2006.01)

(52) U.S. Cl.
  CPC ........... *C04B 38/067* (2013.01); *G01N 29/28* (2013.01); *C01P 2002/02* (2013.01); *C01P 2006/10* (2013.01)

(58) Field of Classification Search
  CPC .............. C01P 2002/02; C01P 2006/10; B06B 1/0677; B06B 1/06; A61B 8/4444; A61B 8/14; A61B 8/4488; A61B 8/4494; H04R 17/00
  See application file for complete search history.

(56) References Cited

U.S. PATENT DOCUMENTS

| | | | |
|---|---|---|---|
| 2009/0062656 | A1 | 3/2009 | Hyuga |
| 2011/0096953 | A1 | 4/2011 | Liu et al. |
| 2011/0240401 | A1* | 10/2011 | Suzuki ..................... H04R 7/02 977/902 |
| 2013/0028831 | A1 | 1/2013 | Neumann et al. |
| 2013/0285174 | A1 | 10/2013 | Sako et al. |
| 2013/0345567 | A1 | 12/2013 | Sudol et al. |
| 2016/0007961 | A1 | 1/2016 | Lee et al. |
| 2017/0125005 | A1* | 5/2017 | Oono ........................ B32B 9/04 |

FOREIGN PATENT DOCUMENTS

| | | |
|---|---|---|
| EP | 2 842 642 A2 | 3/2015 |
| JP | 2009-60501 A | 3/2009 |
| JP | 4319644 B2 | 8/2009 |
| JP | 2010-157926 A | 7/2010 |
| JP | 2013-115537 A | 6/2013 |
| JP | 2013-236262 A | 11/2013 |
| JP | 2015-93012 A | 5/2015 |
| JP | 2015-221214 A | 12/2015 |
| JP | 2016-21737 A | 2/2016 |
| WO | 2013/081915 A2 | 6/2013 |

OTHER PUBLICATIONS

Office Action dated Dec. 14, 2021, issued in counterpart EP application No. 19793954.9. (9 pages).
International Search Report dated May 7, 2019, issued in counterpart International Application No. PCT/JP2019/014535 (2 pages).
Written Opinion in Japanese dated May 7, 2019, issued in counterpart International Application No. PCT/JP2019/014535 (3 pages).

* cited by examiner

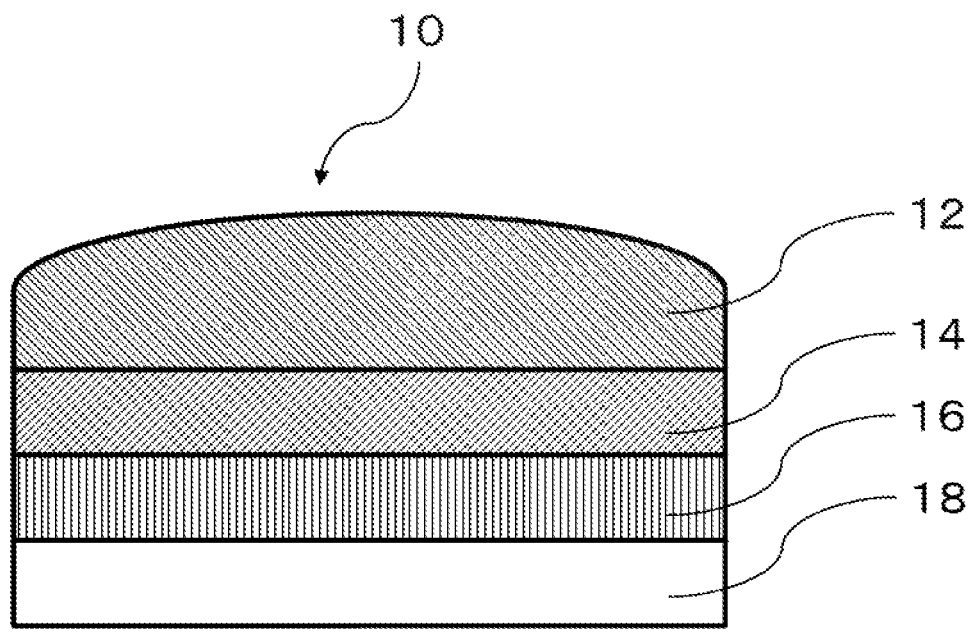

BACKING MATERIAL FOR ULTRASONIC PROBE, METHOD OF MANUFACTURING SAME, AND ULTRASONIC PROBE

FIELD

The present invention relates to a backing member for an ultrasonic probe and a method of manufacturing the same, and an ultrasonic probe.

BACKGROUND

Ultrasonic diagnostic equipment and ultrasonic imaging equipment for medical use transmit ultrasonic signal to an object, and then image the interior of the object by receiving the reflected signal (echo signal) from the object. Arrayed ultrasonic probes with ultrasonic signal transmitting and receiving functions are mainly used for these ultrasonic diagnostic equipment and ultrasonic imaging equipment.

The ultrasonic probe includes, in the order from the object side described above, an acoustic lens, an acoustic matching layer, a piezoelectric element, and a backing member. The backing member constituting such an ultrasonic probe is required to have performance such as good attenuation property for ultrasonic waves for improving sensitivity, and high thermal conductivity for preventing overheating of the piezoelectric element. Various backing members have been proposed.

PTL 1 discloses an ultrasonic probe in which a piezoelectric element, an acoustic matching layer, and an acoustic lens are laminated in this order on a sheet-shaped acoustic backing member. The piezoelectric element and the acoustic matching layer are divided into a plurality in an array shape, and grooves corresponding to the divided portions are formed on the acoustic backing layer. The acoustic backing member comprises an ethylene-vinyl acetate copolymer having a vinyl acetate content of 20 to 80 wt % and a filler material contained in the ethylene-vinyl acetate copolymer, and the acoustic impedance thereof is 2 to 8 MRalys.

In addition, PTL 2 discloses a backing element used in in an ultrasonic probe. The backing element is provided on the opposite side of a transmission direction of ultrasonic waves to an object, with respect to an ultrasonic vibrator for transmitting ultrasonic waves to the object. The backing element comprises a plate-like backing member, a thermal conductor and a thermal conductive plate made of a material having a higher thermal conductivity than the backing member. The thermal conductor is embedded in the backing member and formed in a columnar shape so as to reach both plate surfaces of the backing member. The thermal conductive plate is provided on at least the side of the ultrasonic vibrator of both plate surfaces of the backing member.

CITATION LIST

Patent Literature

[PTL 1] JP 4319644 B
[PTL 2] JP 2013-115537 A

SUMMARY

Technical Problem

Depending on the application of the backing member, it may be required to be able to chop the material with a small pitch. However, the backing members described in PTL 1 and 2 are composed of a resin and a filler, and when an attempt is made to chop a material for such a backing member, the resin is then deformed by heat, and as a result, a desired shape cannot be obtained in some cases.

Further, although the backing member composed of a resin and a filler can provide good attenuation property for ultrasonic waves can be obtained, it was necessary to provide a separate element for thermal conductivity.

Therefore, there is a need to provide a novel backing member that combines good attenuation property for ultrasonic waves, good workability, good thermal conductivity, and good aging resistance.

Solution to Problem

As a result of intensive investigations, the present inventors have discovered that the above-described problems can be solved by the following means and have accomplished the present invention. More specifically, the present invention is as follows:

<Aspect 1> A backing member for an ultrasonic probe substantially composed of porous amorphous carbon.

<Aspect 2> The backing member according to aspect 1, wherein the acoustic impedance thereof is 2.0-5.8 Mrayl.

<Aspect 3> The backing member according to aspect 1 or 2, further comprising a carbonaceous filler, which is dispersed in said amorphous carbon.

<Aspect 4> The backing member according to aspect 3, wherein the carbonaceous filler is at least one selected from the group consisting of carbon fibers and carbon particles.

<Aspect 5> The backing member according to any one of aspects 1 to 4, wherein the density thereof is 1.5 g/cm$^3$ or less.

<Aspect 6> An ultrasonic probe comprising an acoustic lens, an acoustic matching layer, a piezoelectric element, and the backing member according to any one of aspects 1 to 5, in this order.

<Aspect 7> A method of manufacturing a backing member according to any one of aspects 1 to 5, comprising
 dispersing a pore forming material in a carbon precursor, and then
 heat-treating the carbon precursor together with the pore forming material under a non-oxidizing atmosphere to carbonize the carbon precursor.

<Aspect 8> The method for manufacturing a backing member according to aspect 7, wherein the pore forming material is at least one selected from the group consisting of alcohols, ethers, alcohol-based polymers, ether-based polymers, and acrylic-based polymers.

Advantageous Effects of Invention

According to the present invention, it is possible to provide a novel backing member which combines good attenuation property for ultrasonic waves, good workability, good thermal conductivity, and good aging resistance.

BRIEF DESCRIPTION OF DRAWINGS

FIG. 1 is a conceptual diagram of an ultrasonic probe of the present invention.

DESCRIPTION OF EMBODIMENTS

<<Backing Member for Ultrasonic Probe>>

The backing member for ultrasonic probe of the present invention is substantially composed of porous amorphous carbon.

In the present specification. "substantially composed of" means, for example, that the porous amorphous carbon occupies 50 volume % or more, 60 volume % or more, 70 volume % or more, 80 volume % or more, or 90 volume % or more, and 100 volume % or less, 98 volume % or less, or 95 volume % or less of the backing member for ultrasonic probe.

The backing member for ultrasonic probe of the present invention having the above-described configuration can satisfactorily attenuate ultrasonic waves. More specifically, the attenuation property for ultrasonic waves of the backing member for an ultrasonic probe according to JIS Z 2354-2012 can be −10 dB/cm or less, −13 dB/cm or less, or −15 dB/cm or less, and can be −30 dB/cm or more, −28 dB/cm or more, −25 dB/cm or more, −23 dB/cm or more, or −20 dB/cm or more.

Without wishing to be bound by theory, it is believed that the backing member for ultrasonic probe, due to its porosity, causes the ultrasonic waves to diffusely reflect internally, resulting in the attenuation property for ultrasonic waves described above. Further, it is considered that the backing member for the ultrasonic probe further has a high rigidity as a whole backing member, as well as good thermal conductivity and good aging resistance, and thus the sag when cut is suppressed, since the backing member for the ultrasonic probe is substantially composed of amorphous carbon.

The acoustic impedance of the present invention backing member for ultrasonic probe may be 2.0 Mrayl or more, 2.5 Mrayl or more, 3.0 Mrayl or more, or 3.5 Mrayl or more, and the acoustic impedance may be 5.5 Mrayl or less, 5.3 Mrayl or less, 5.0 Mrayl or less, 4.8 Mrayl or less, 4.5 Mrayl or less, or 4.0 Mrayl or less.

The acoustic impedance is obtained by the following equation.

$$\text{Acoustic Impedance } (Z: \text{Mrayl}) = \text{Density } (\rho: g/cm^3) \times \text{Speed } (C: m/sec)/10^3$$

The above-mentioned sound velocity may be, for example, a sound velocity measured in accordance with IS Z 2353-2003.

The density of the backing member for ultrasonic probe having the above-mentioned configuration can be 1.55 g/cm$^3$ or less. The density can be less than 1.50 g/cm$^3$, less than 1.45 g/cm$^3$, or less than 1.40 g/cm$^3$, and more than 0.90 g/cm$^3$, more than 0.95 g/cm$^3$, more than 1.00 g/cm$^3$, more than 1.10 g/cm$^3$, or more than 1.15 g/cm$^3$.

Further, the backing member for an ultrasonic probe of the present invention may comprise an optional carbonaceous filler.

Hereinafter, each component of the present invention will be described.

<Porous Amorphous Carbon>

The porous amorphous carbon is formed, for example, by carbonizing a carbon precursor and a pore forming material under a non-oxidizing atmosphere. The detail thereof, will be described in "Method for manufacturing a backing member".

<Carbonaceous Filler>

The carbonaceous filler may be carbon fibers and/or carbon particles dispersed in the amorphous carbon.

Examples of carbon fibers include, but are not limited to, milled fibers, and chopped fibers. These may be used alone or in combination.

The average length of the carbon fibers may be 1 μm or more, 3 μm or more, 5 μm or more, 10 μm or more, or 15 μm or more, and 100 μm or less, 70 μm or less, 50 μm or less, or 30 μm or less.

Examples of the carbon particles include graphene, carbon nanotubes, graphite, and carbon black. These may be used alone or in combination.

The shape of the carbon particles is not particularly limited, and may be, for example, a flat shape, an array shape, a spherical shape, or the like.

The average particle diameter of the carbon particles may be 100 m or more, 200 nm or more, 300 nm or more, 500 nm or more, 700 nm or more, 1 μm or more, 2 μm or more, or 3 μm or more, and 20 μm or less, 15 μm or less, 10 μm or less, or 7 μm or less. In the present specification, the average particle diameter means the median diameter (D50) calculated by the volume standard in the laser diffraction method.

The content of the carbonaceous filler in the backing member for ultrasonic probe may be 30 mass % or less, 25 mass % or less, 20 mass % or less, or 15 mass % or less, and can be 5 mass % or more, 7 mass % or more, or 10 mass % or more, based on the mass of the entire backing member for ultrasonic probe. When the content of the carbonaceous filler is 30 mass % or less, forming of the backing member for an ultrasonic probe can be more easily carried out. When the content of the carbonaceous filler is 5 mass % or more, good mechanical properties of the backing member for an ultrasonic probe can be achieved.

<<Ultrasonic Probe>>

As shown in FIG. 1, the ultrasonic probe 10 of the present invention comprises an acoustic lens 12, an acoustic matching layer 14, a piezoelectric element 16, and a backing member 18 as described above in this order.

<Acoustic Lens>

Acoustic lenses are generally used to focus the ultrasonic beam by using refraction and improve the resolution of the ultrasonic beam.

In the present invention, as a material constituting an acoustic lens, for example, a homopolymer such as a conventionally known silicone rubber, a fluorosilicone rubber, a polyurethane rubber, or an epichlorohydrin rubber, a copolymer rubber such as a ethylene-propylene copolymer rubber obtained by copolymerizing ethylene and propylene, or the like can be used.

<Piezoelectric Element>

Piezoelectric elements generally have electrodes and piezoelectric materials, and are elements capable of converting electrical signals into mechanical vibrations and mechanical vibrations into electrical signals, and thereby capable of transmitting and receiving ultrasonic waves.

(Piezoelectric Material)

The piezoelectric material may be a material capable of converting electrical signals into mechanical vibrations and mechanical vibrations into electrical signals. As the piezoelectric material, for example, lead zirconate titanate (PZT)-based ceramics, piezoelectric ceramics such as PbTiO$_3$-based ceramics, organic polymer piezoelectric materials such as vinylidene fluoride (VDF)-based polymers, vinylidene cyanide (VDCN)-based polymers, quartz, Rochelle salts, and the like can be used.

Examples of the vinylidene fluoride (VDF)-based polymer include polyvinylidene fluoride (PVDF), polyvinylidene fluoride-3 ethylene fluoride (P (VDF-TrFE)), and the like. Examples of the vinylidene cyanide (VDCN)-based polymer include polyvinylidene cyanide (PVDCN) and vinylidene cyanide based copolymers.
(Electrode)

As the electrode, for example, gold (Au), platinum (Pt), silver (Ag), palladium (Pd), copper (Cu), aluminum (Al), nickel (Ni), tin (Sn), or the like can be used.

<Acoustic Matching Layer>

The acoustic matching layer generally matches the acoustic impedance between the ultrasonic transducer and a test object, and is made of a material having an acoustic impedance intermediate between the ultrasonic transducer and the test object.

As materials used for the acoustic matching layers, aluminum, aluminum alloy (e.g., AL-Mg alloy), magnesium alloy, Macor glass, glass, fused silica, copper graphite, polyethylene (PE), polypropylene (PP), ABC resin, ABS resin, AAS resin, AES resin, nylon (PA6, PA6-6), PPO (polyphenylene oxide), PPS (polyphenylene sulfide: glass fiber can further be contained), PPE (polyphenylene ether), PEEK (polyether ether ketone), PAI (polyamide imide), PETP (polyethylene terephthalate), PC (polycarbonate), epoxy resin, urethane resin, and the like can be used.

The acoustic matching layer may be a single layer or a multiple layer.

<<Method for Manufacturing a Backing Member>>

The method of the present invention for manufacturing a backing member comprises
  dispersing a pore forming material in a carbon precursor to prepare a composition for a backing member, and then
  heat-treating the composition for the backing member under a non-oxidizing atmosphere to carbonize the carbon precursor.

The density of the backing member manufactured as described above may be 1.55 g/cm$^3$ or less. The density can be less than 1.50 g/cm$^3$, less than 1.45 g/cm$^3$, or less than 1.40 g/cm$^3$, and more than 0.90 g/cm$^3$, more than 0.95 g/cm$^3$, more than 1.00 g/cm$^3$, more than 1.10 g/cm$^3$, or more than 1.15 g/cm$^3$.

The heat treatment can be carried out, for example, at a temperature of 600° C. or higher, 650° C. or higher, 700° C. or higher, 750° C. or higher, 800° C. or higher, 850° C. or higher, 900° C. or higher, and 1200° C. or lower, 1150° C. or lower, 1100° C. or lower, 1050° C. or lower, or 1000° C. or lower.

<Preparation of Composition for Backing Member>

Preparation of a composition for a backing member is carried out by dispersing a pore forming material in a carbon precursor. Dispersion can be carried out, for example, by stirring the carbon precursor and the pore forming material using a known stirrer.

The content of the pore forming material in the composition for a backing member may be 30 mass % or less, 25 mass % or less, 20 mass % or less, or 15 mass % or less, based on the mass of the entire composition for a backing member, and may be 5 mass % or more, 7 mass % or more, or 10 mass % or more.

In the composition for backing member, an optional carbonaceous filler may be further dispersed. In this case, the content of the carbonaceous filler may be 30 mass % or less, 25 mass % or less, 20 mass % or less, or 15 mass % or less, based on the mass of the entire composition for the backing member, and may be 5 mass % or more, 7 mass % or more, 9 mass % or more, or 10 mass % or more. When the content of the carbonaceous filler is 30 mass % or less, forming of the backing member can be more easily carried out. Further, when the content of the carbonaceous filler is 5 mass % or more, good mechanical properties of the backing member can be achieved. As the carbonaceous filler, the carbonaceous filler recited with respect to a backing member for an ultrasonic probe can be used.

In addition, in order to fix the pore forming material in the carbon precursor before the heat treatment, an optional curing agent may be contained in the composition for the backing member. In this case, the content of the curing agent may be 5 mass % or less, 3 mass % or less, or 1 mass % or less, and may be more than 0 mass %, 0.3 mass % or more, or 0.5 mass % or more.

(Carbon Precursors)

As the carbon precursor, for example phenolic resin, furan resin, imide resin, epoxy resin, and an unsaturated polyester resin or the like may be used. These may be used alone or as a mixture of 2 or more thereof.

(Pore Forming Material)

The pore forming material can disappear by heat-treating the composition for the backing member to form pores in the backing member.

As such a pore forming material, for example, alcohols, ethers, and polymers may be used. These may be used alone or as a mixture thereof.

As the alcohols, for example, monohydric alcohols such as methanol, ethanol, propanol, and vinyl alcohol, polyols such as ethylene glycol, and the like can be used.

As the ethers, for example, dimethyl ether, diethyl ether, and diethylene glycol can be used.

As the polymer, for example, an alcohol-based polymer, a ether-based polymer, and an acrylic polymer can be used.

As the alcohol-based polymer, for example, polyvinyl alcohol, and butyral resin can be used.

As the ether-based polymer, polyethylene glycol, polypropylene glycol, polybutylene glycol, or the like can be used.

As the acrylic-based polymer, for example, poly(meth)acrylic acid, polymethyl(meth)acrylate, polyethyl(meth)acrylate, polypropyl(meth)acrylate, polybutyl(meth)acrylate, polyisobutyl acrylate, polypentyl(meth)acrylate, polyhexyl(meth)acrylate, poly-2-ethylhexyl(meth)acrylate, or the like can be used, and among them, polymethyl methacrylate is preferably used from the viewpoint of the formation efficiency of pores.

(Curing Agent)

As the curing agent, for example, p-toluenesulfonic acid or the like can be used.

EXAMPLES

The present invention will be specifically described by way of Examples and Comparative Examples, but the present invention is not limited thereto.

<<Preparation of Backing Material>>

Example 1

70 mass parts of furan resin (Hitachi Chemical Co., Ltd.) as a carbon precursor, 10 mass parts of graphite (scaly graphite, Nippon Graphite Industry Co., Ltd., average particle diameter: 5 μm) as a carbonaceous filler, 20 mass parts of polymethyl methacrylate (PMMA)(Sekisui Chemical Industries, Ltd., average particle diameter: 10 μm) as a pore forming material, and 1 mass parts of p-toluenesulfonic acid as a curing agent were sufficiently stirred using a stirrer, and subjected to a vacuum defoaming operation to prepare a composition for a backing member.

The prepared composition for backing member was then poured into a 5 mm thick mold and cured, and then heat-treated at a temperature of 1000° C. under a nitrogen atmosphere to obtain a backing member of Example 1 having a thickness of 4 mm.

Example 2

A backing member of Example 2 having a thickness of 4 mm was obtained in the same manner as in Example 1, except that the content of furan resin was 80 mass parts and the content of polymethyl methacrylate was 10 mass parts.

Example 3

A backing member of Example 3 having a thickness of 4 mm was obtained in the same manner as in Example 2, except that 10 mass parts of ethylene diethylene glycol was used instead of polymethyl methacrylate as the pore forming material.

Example 4

A backing member of Example 4 having a thickness of 4 mm was obtained in the same manner as in Example 1 except that 10 mass parts of ethanol and 10 mass parts of butyral resin (Sekisui Chemical Co., Ltd.) were used instead of polymethyl methacrylate as the pore forming material.

Example 5

A backing member of Example 5 having a thickness of 4 mm was obtained in the same manner as in Example 1 except that 5 mass parts of ethanol and 5 mass parts of butyral resin (Sekisui Chemical Co., Ltd.) were used instead of polymethyl methacrylate as the pore forming material.

Example 6

A backing member of Example 6 having a thickness of 4 mm was obtained in the same manner as in Example 5, except that 5 mass parts of diethylene glycol was used instead of ethanol as the pore forming material.

Comparative Example 1

A backing member of Comparative Example 1 having a thickness of 4 mm was obtained in the same manner as in Example 1, except that the content of furan resin was 90 mass parts and no pore forming material was used.

Comparative Example 2

Acrylic resin plate having a thickness of 3 mm (Misumi Co., Ltd.) was the backing member of Comparative Example 2.

<<Evaluation>>

The manufactured backing member was cut to a size of 30 mm×30 mm×3 mm, and the density was calculated by measuring the mass, and the following evaluation was carried out.

<Measurement of Sound Velocity and Calculation of Acoustic Impedance>

In accordance with JIS Z 2353-2003, the sound velocity in the interior of each backing member manufactured was measured at 25° C. using a sing-around type sound velocity measuring device. The calculated density and measured sound velocity were used to calculate the acoustic impedance.

<Evaluation of Attenuation Property for Ultrasonic Waves>

In accordance with JIS Z 2354-2012, 25° C. water was filled in the water tank, then an ultrasonic wave of 1 MHz was generated in the water by an ultrasonic pulsar receiver JSR DPR500, the attenuation property for ultrasonic waves in the interior of each backing member was evaluated by measuring the magnitude of the amplitude before and after the ultrasonic wave penetrates the backing member.

<Evaluation of Workability>

Each of the manufactured backing members was cut with a rotary cutter, and the state of the cross-section was visually observed. The evaluation criteria are as follows.

A: There was no sag in the cross section.
B: A sag was observed in the cross section.

<Evaluation of Thermal Conductivity>

A laser flash thermophysical property measuring device (LFA457, NETZSCH Co., Ltd.) was used to measure the thermal conductivity in the thickness direction of the manufactured backing member.

The results are given in Table 1.

TABLE 1

| | | Configuration Composition for backing member | | | | | | |
|---|---|---|---|---|---|---|---|---|
| | | Carbon precursor | | Pore forming material | | Carbonaceous filler | | Curing agent | |
| | | Type | Content (weight parts) | Type | Content (weight parts) | Type | Content (weight parts) | Type | Content (weight parts) |
| Ex.1 | Furan Resin | 70 | PMMA | 20 | Graphite | 10 | p-toluene Sulfonic acid | 1 |
| Ex.2 | Furan Resin | 80 | PMMA | 10 | Graphite | 10 | p-toluene Sulfonic acid | 1 |
| Ex.3 | Furan Resin | 80 | Ethylene Glycol | 10 | Graphite | 10 | p-toluene Sulfonic acid | 1 |
| Ex.4 | Furan Resin | 70 | Ethanol Butyral Resin | 10 10 | Graphite | 10 | p-toluene Sulfonic acid | 1 |

TABLE 1-continued

| | | | | | | | | | |
|---|---|---|---|---|---|---|---|---|---|
| Ex.5 | Furan Resin | 80 | Ethanol<br>Butyral Resin | 5<br>5 | Graphite | 10 | p-toluene Sulfonic acid | 1 |
| Ex.6 | Furan Resin | 80 | Diethylene Glycol<br>Butyral Resin | 5<br>5 | Graphite | 10 | p-toluene Sulfonic acid | 1 |
| Comp Ex.1 | Furan Resin | 90 | — | — | Graphite | 10 | p-toluene Sulfonic acid | 1 |
| Comp Ex.2 | | | | | (Acrylic resin) | | | |

| | Configuration Heat treatment Temperature (° C.) | Density (g/cm³) | Sound velocity (m/s) | Impedance Acoustic (Mrayl) | Evaluation Ultrassonic Attenuation (dB/cm) | Work-ability | Thermal conductivity (W/m · k) |
|---|---|---|---|---|---|---|---|
| Ex.1 | 1000 | 1.23 | 2500 | 3.1 | −18 | A | 4.7 |
| Ex.2 | 1000 | 1.36 | 3000 | 4.1 | −13 | A | 4.9 |
| Ex.3 | 1000 | 1.37 | 3500 | 4.8 | −11 | A | 5.0 |
| Ex.4 | 1000 | 1.15 | 2600 | 3.0 | −23 | A | 5.1 |
| Ex.5 | 1000 | 1.38 | 3300 | 4.6 | −23 | A | 5.2 |
| Ex.6 | 1000 | 1.38 | 3650 | 5.0 | −11 | A | 5.0 |
| Comp Ex.1 | 1000 | 1.58 | 3750 | 5.9 | −9 | A | 5.2 |
| Comp Ex.2 | (Acrylic resin) | 1.18 | 2700 | 3.2 | −15 | B | 0.2 |

From Table 1, it can be understood that the backing member of Examples 1-6, which was substantially composed of porous amorphous carbon, is a backing member which combines good attenuation property for ultrasonic waves, good workability, and good thermal conductivity.

On the other hand, the backing member of Comparative Example 1, which was substantially composed of amorphous carbon that was not porous, had good workability and thermal conductivity, but did not have good attenuation property for ultrasonic waves.

The backing member of Comparative Example 2, which was composed of an acrylic resin, had good attenuation property for ultrasonic waves, but did not have good workability and thermal conductivity.

In addition, although not shown in the table, the backing members of Examples 1-6 and Comparative Example 1, which was substantially composed of amorphous carbon, may naturally be predicted to have good aging resistance due to the stability of the amorphous carbon.

REFERENCE SIGNS LIST

10 Ultrasonic probe
12 Acoustic lens
14 Acoustic matching layer
16 Piezoelectric element
18 Backing member

What is claimed is:

1. A backing member for an ultrasonic probe substantially composed of porous amorphous carbon, wherein the backing member is provided on an opposite side of a transmission direction of ultrasonic waves to an object, with respect to a piezoelectric element for transmitting ultrasonic waves to the object, a density of the backing member is more than 0.90 g/cm³, and attenuation property for ultrasonic waves of the backing member according to JIS Z 2354-2012 is −10 dB/cm or less.

2. The backing member as claimed in claim 1, wherein the acoustic impedance thereof is 2.0-5.8 Mrayl.

3. The backing member as claimed in claim 1, further comprising a carbonaceous filler, which is dispersed in said amorphous carbon.

4. The backing member as claimed in claim 3, wherein the carbonaceous filler is at least one selected from the group consisting of carbon fibers and carbon particles.

5. The backing member as claimed in claim 1, wherein the density thereof is 1.5 g/cm³ or less.

6. An ultrasonic probe comprising an acoustic lens, an acoustic matching layer, a piezoelectric element, and the backing member as claimed in claim 1, in this order.

7. A method of manufacturing a backing member as claimed in claim 1, comprising
dispersing a pore forming material in a carbon precursor, and then
heat-treating the carbon precursor together with the pore forming material under a non-oxidizing atmosphere to carbonize the carbon precursor.

8. The method for manufacturing a backing member as claimed in claim 7, wherein the pore forming material is at least one selected from the group consisting of alcohols, ethers, alcohol-based polymers, ether-based polymers, and acrylic-based polymers.

* * * * *